United States Patent
Fomina et al.

(10) Patent No.: US 10,843,192 B2
(45) Date of Patent: *Nov. 24, 2020

(54) INTEGRATION OF ELECTROCHEMICAL PH MODULATION WITH LAB ON A CHIP TECHNOLOGIES

(71) Applicant: Robert Bosch GmbH, Stuttgart (DE)

(72) Inventors: Nadezda Fomina, Redwood City, CA (US); Christopher Johnson, San Carlos, CA (US); Habib Ahmad, Sunnyvale, CA (US); Christoph Lang, Cupertino, CA (US); Franz Laermer, Weil der Stadt (DE)

(73) Assignee: ROBERT BOSCH GMBH, Stuttgart (DE)

( * ) Notice: Subject to any disclaimer, the term of this patent is extended or adjusted under 35 U.S.C. 154(b) by 198 days.

This patent is subject to a terminal disclaimer.

(21) Appl. No.: 15/773,292

(22) PCT Filed: Nov. 4, 2016

(86) PCT No.: PCT/IB2016/001691
§ 371 (c)(1),
(2) Date: May 3, 2018

(87) PCT Pub. No.: WO2017/077384
PCT Pub. Date: May 11, 2017

(65) Prior Publication Data
US 2018/0318834 A1 Nov. 8, 2018

Related U.S. Application Data

(60) Provisional application No. 62/250,906, filed on Nov. 4, 2015.

(51) Int. Cl.
*C12Q 1/6825* (2018.01)
*B01L 3/00* (2006.01)
*C12N 15/10* (2006.01)
*G01N 27/327* (2006.01)

(52) U.S. Cl.
CPC ....... *B01L 3/502715* (2013.01); *B01L 3/5027* (2013.01); *C12N 15/1003* (2013.01); *C12Q 1/6825* (2013.01); *B01L 2300/087* (2013.01); *B01L 2400/046* (2013.01); *C12Q 2527/119* (2013.01); *C12Q 2565/607* (2013.01); *G01N 27/3277* (2013.01)

(58) Field of Classification Search
CPC ............ B01L 3/502715; B01L 3/5027; B01L 2400/046; B01L 2300/087; C12Q 1/6825; C12Q 2565/607; C12Q 2527/119; C12N 15/1003; G01N 27/3277
See application file for complete search history.

(56) References Cited

U.S. PATENT DOCUMENTS

| 9,910,008 B2* | 3/2018 | Johnson ............. G01N 27/3276 |
| 2014/0008244 A1* | 1/2014 | Kavusi ................... G01N 33/50 205/777.5 |
| 2014/0322100 A1 | 10/2014 | Laermer et al. |
| 2017/0008825 A1 | 1/2017 | Johnson et al. |
| 2017/0010238 A1 | 1/2017 | Johnson et al. |

FOREIGN PATENT DOCUMENTS

| DE | 102013200466 A1 | 7/2014 |
| WO | 2014/152325 | 9/2014 |

OTHER PUBLICATIONS

Lee, Hun Joo, et al. "Electrochemical Cell Lysis Device for DNA Extraction." The Royal Society of Chemistry, vol. 10, No. 5, 2010, pp. 626-633., doi:10.1039/b916606h. (Year: 2010).*
Nan, Lang, et al. "Emerging Microfluidic Devices for Cell Lysis: a Review." The Royal Chemistry Society, vol. 14, No. 6, 2014, pp. 1060-1073., doi:10.1039/c3lc51133b. (Year: 2014).*
Birnboim et al., "A rapid alkaline extraction procedure for screening recombinant plasmid DNA," Nucleic Acids Res. 7:1513-1518 (1979).
Whitten et al., "Local conformational fluctuations can modulate the coupling between proton binding and global structural transitions in proteins," Proc. Natl. Acad. Sci. U. S. A. 102,4282-4287 (2005).
Zhang et al., "Optimization of DNA Hybridization Efficiency by pH-Driven Nanomechanical Bending," Langmuir, 28 (15), pp. 6494-6501 (2012).
International Search Report dated Apr. 4, 2017 of the corresponding International Application PCT/IB2016/001691 filed Nov. 4, 2016.
Hun Joo Lee et al., "Electrochemical cell lysis device for DNA extraction", Lab on a Chip, Dec. 17, 2009, vol. 10, No. 5, , pp. 626-633.
Lang Nan et al., "Emerging microfluidic devices for cell lysis: a review", Lab on a Chip, Dec. 4, 2013, vol. 14, No. 6, pp. 1060-1073.
European Office Action dated Jun. 6, 2019 in European patent Application No. 16 819 163.3.

* cited by examiner

*Primary Examiner* — Jennifer Wecker
*Assistant Examiner* — Michael Paul Shimek
(74) *Attorney, Agent, or Firm* — Norton Rose Fulbright US LLP; Gerard Messina; Aaron Grunberger

(57) ABSTRACT

At least one electrode is integrated on a lab on a chip cartridge in a sample preparation chamber of the cartridge, a DNA hybridization chamber of the cartridge, a protein assay chamber of the cartridge, and/or a detection chamber of the cartridge, for example, where the electrode is used to generate pH electrochemically in order to activate, deactivate, or intermediately attenuate an enzyme's activity on demand, in order to increase the fidelity of analyte detection, for cell lysis, for protein extraction, for DNA dehybridization, for primer hybridization control, for sample pre concentration, and/or for washing to remove non target species.

4 Claims, No Drawings

INTEGRATION OF ELECTROCHEMICAL PH MODULATION WITH LAB ON A CHIP TECHNOLOGIES

CROSS-REFERENCE TO RELATED APPLICATION

The present invention is the national stage of International Patent Application No. PCT/IB2016/001691, filed on Nov. 4, 2016, which claims the benefit of U.S. Provisional Patent Application Ser. No. 62/250,906, filed Nov. 4, 2015, the content of each of which are incorporated herein by reference in their entireties.

DETAILED DESCRIPTION

The present invention is directed to electronic control of pH of a solution close to electrode surfaces, and to integration of an electrochemical pH modulation technology (for example as described in U.S. patent application Ser. Nos. 14/792,576 now U.S. Pat. No. 10,379,080 and 14/792,553 now U.S. Pat. No. 10,011,549, which are incorporated herein by reference in their entireties, and much of the disclosure of which is reproduced below) with lab on a chip (LOC) technology (for example as described in U.S. patent application Ser. No. 14/254,968 now U.S. Pat. No. 10,295,441 and German Pat. App. No. DE102013200466.4, which are incorporated herein by reference in their entirety). There are multiple modes of integration, in example embodiments, for different aspects of the two technologies.

SAMPLE PREPARATION APPLICATIONS

In an example embodiment, electrochemical pH modulation is performed to change pH as a method to lyse cells, e.g., as a method to break down the cell wall of bacteria by alkaline lysis (see Birnboim et al., "A rapid alkaline extraction procedure for screening recombinant plasmid DNA," Nucleic Acids Res. 7:1513-1518 (1979)) by generating a higher pH using an electrode, either using electroactive redox species or water hydrolysis, and this is performed on a LOC chip. This process can be used separately or in combination with thermal lysis. In the case of water hydrolysis, symmetric alternating current (AC) can be used to prevent evolution of H2 or O2 bubbles.

In an example embodiment, there is integration of (a) an affinity substrate with (b) washing followed by (c) pH actuated elution by electrochemical pH modulation, all on a LOC chip. An example includes silica beads to adsorb DNA onto the surface, followed by changing the pH to promote DNA release for further downstream testing.

Hybridization Applications

In an example embodiment, electrochemical pH modulation is performed on a LOC chip as a method to facilitate hybridization by disrupting the hydration shell around DNA as an alternative to using high salt concentrations or mercaptohexanol or other hybridization aids (see Whitten et al., "Local conformational fluctuations can modulate the coupling between proton binding and global structural transitions in proteins," Proc. Natl. Acad. Sci. U.S.A 102, 4282-4287 (2005)).

For DNA microarrays, electrochemical pH modulation on a LOC chip (such as one that includes a microarray) can be used to tune the hybridization to probe DNA strands, to reduce non-target hybridization.

During polymerase chain reaction (PCR) cycling, electrochemical pH modulation on a LOC chip can be used to reduce hybridization of primers to non-target DNA strands.

Protein Assay Applications

In an example embodiment, electrochemical pH modulation is used in a LOC cartridge (for example as described in U.S. patent application Ser. No. 14/254,968 and German Pat. App. No. DE102013200466.4).

Detection Applications

The activity of most enzymes varies as a function of pH (Zhang et al., "Optimization of DNA Hybridization Efficiency by pH-Driven Nanomechanical Bending," Langmuir, 28 (15), pp. 6494-6501 (2012)). In an example embodiment, for chemiluminescent assays, electrochemical pH modulation on a LOC chip is used to change pH in order to activate or deactivate an enzyme, enabling continuous signal readout, as opposed to end point detection (standard for chemiluminescent assays). Reducing the activity of an enzyme (i.e., partial deactivation) by the electrochemical pH modulation can also be used to extend dynamic range.

What is claimed is:

1. An apparatus comprising:
   a lab on a chip cartridge on which at least one electrode is integrated,
   wherein:
      the at least one electrode is integrated in at least one of a sample preparation chamber of the cartridge, a DNA hybridization chamber of the cartridge, a protein assay chamber of the cartridge, and a detection chamber of the cartridge; and
      one or more of the at least one electrode is configured to generate pH electrochemically and control pH of a solution within a distance of about 1 cm of the one or more of the at least one electrode.

2. The apparatus of claim 1, wherein one or more of the at least one electrode is used to generate pH electrochemically for one or more of cell lysis, protein extraction, DNA dehybridization, primer hybridization control, sample pre concentration, and washing to remove non target species.

3. The apparatus of claim 1, wherein one or more of the at least one electrode is used to generate pH electrochemically in order to activate, deactivate, or intermediately attenuate an enzyme's activity on demand.

4. The apparatus of claim 1, wherein one or more of the at least one electrode is used to generate pH electrochemically in order to increase the fidelity of analyte detection.

* * * * *